United States Patent [19]

Cervelli et al.

[11] Patent Number: 5,443,975
[45] Date of Patent: Aug. 22, 1995

[54] METHOD OF BINDING ENZYMES TO SINTERED EXPANDED CLAYS

[75] Inventors: Stefano Cervelli, Pisa; Vincenzo Capuano, Anguillara Sabazia, both of Italy

[73] Assignees: Ente Per Le Nuove Technologie, L'Energia E L'Ambiente (ENEA); Consiglio Nazionale Delle Ricerche, both of Rome, Italy

[21] Appl. No.: 986,045

[22] Filed: Dec. 10, 1992

Related U.S. Application Data

[63] Continuation-in-part of Ser. No. 712,878, Jun. 11, 1991, abandoned.

[30] Foreign Application Priority Data

Jun. 13, 1990 [IT]  Italy .................................. 48058/90

[51] Int. Cl.$^6$ ................ C12N 11/18; C12N 11/14; C12N 11/08; C12N 11/04
[52] U.S. Cl. .............................. 435/175; 435/176; 435/180; 435/181; 435/182; 435/262.5
[58] Field of Search ............... 435/174, 175, 176, 177, 435/180, 181, 182, 262.5

[56] References Cited

U.S. PATENT DOCUMENTS

| | | | |
|---|---|---|---|
| 2,717,852 | 9/1955 | Stone | 435/176 X |
| 3,556,945 | 1/1971 | Messing | 435/176 |
| 3,933,589 | 1/1976 | Keyes | 435/176 |
| 3,982,997 | 9/1976 | Eaton et al. | 435/176 X |
| 4,226,938 | 10/1980 | Yoshida et al. | |
| 4,585,738 | 4/1986 | Roland | 435/176 |

*Primary Examiner*—David M. Naff
*Attorney, Agent, or Firm*—Stevens, Davis, Miller & Mosher

[57] ABSTRACT

Enzymes, cells and/or cellular organelles are bound to an insoluble sintered expanded clay support matrix for catalyzing transformations of agriculture and industrial residues in soil and in other environments. In one embodiment, an enzyme is absorbed by the sintered expanded clay support matrix and a phenolic monomer is polymerized or copolymerized on the support matrix containing the bound enzyme. In another embodiment, an enzyme different from the enzyme absorbed by the support matrix is combined with the phenolic monomer and a copolymer of enzyme and phenolic monomer is formed on the support matrix containing the bound enzyme. The phenolic monomer is preferably catechol, pyrogallic acid and/or resorcinol. Polymerization or copolymerization of the phenolic monomer is catalyzed by enzyme catalysis with laccase or tyrosinase or peroxidase in combination with hydrogen peroxide, by inorganic catalysis with ammonium persulfate or manganese dioxide, or by organic catalysis with N,N,N',N' tetramethyl-ethylene-diamine (TEMED).

12 Claims, 1 Drawing Sheet

POLYMER

COPOLYMER

BIOLOGICAL CATALYTIC ACTIVITIES

METHOD OF BINDING ENZYMES TO SINTERED EXPANDED CLAYS

This application is a Continuation-on-part of application Ser. No. 07/712,878, filed Jun. 11, 1991, now abandoned.

The present invention relates to a method for binding biological catalytic activities (enzymes, cells, cellular organelles) to substrates formed of sintered expanded clays as well as the products obtained from said method which can be used in agriculture as catalysts of processes adapted to change and improve the efficiency of not very fertile lands, in the decontamination operations, in the city and industrial waste dumps, in the industrial processes for depurating mud and waste water, and generally in any field where transformation reactions should be catalyzed.

BACKGROUND OF THE INVENTION

Transformation of agricultural, industrial and city wastes is one of the most delicate problems to be solved at present. Hitherto made attempts have been aiming at the solution of particular cases. Moreover, the biotechnology applied to this field has not given any expected result so far because, even if genetically modified microorganisms having the capability of degrading the poison and yet harmful waste materials have been developed, the use of such microorganisms in agriculture or in decontamination operations is subjected to the release thereof into the environment, which is causing many problems also due to the risk of transferring the modified genetic characteristics to other organisms.

In contrast, there is provided according to the present invention the use of one or more enzymes bound on materials which are not expensive, becomes integrated in the application environment, and do not affect but positively modify the catalytic activities by protecting them with the time and in the operation fields. The use of such bound biological catalytic activities, even if they are obtained from genetically modified microorganisms, does not imply the above mentioned problems nor meet with application difficulties.

Several techniques of binding enzymes and cells have been known for many years, such techniques being aimed at the binding or localization of such enzymes during continuous catalytic processes.

The purpose of such binding techniques has been achieved either by covalent bonding with insoluble or made insoluble "functionalized" polymers, or by the absorption on organic or inorganic insoluble substrates, or by the entrapping within gelatinous matrices or semipermeable microcapsules.

The essential reasons leading to the production and the use of bound enzymes are three: the first one is that the enzymes can have in this way a considerable operative advantage over the free enzymes; the second one is that the chemical and physical characteristics of the enzymes can be selectively modified; the third one is that the enzymes can act as models of natural systems and enzymatic activities bound to the walls or to cellular organelles.

Such preparations have the operative advantages of being re-usable as well as being used both in static and dynamic systems, interrupting immediately and totally any catalytic reaction, forming under control the requested products, allowing simpler industrial plants of different types to be designed as high operating temperatures and pressures are not requested, and finally achieving a greater efficiency in those processes requiring several reactions.

Changing or at any rate modifying the reactivity of the enzymes is bound to the binding process, especially if the latter is a chemical process. In fact the methods based upon a chemical binding process depend on the reactivity of some functional groups of the enzymes. As such functional groups are eliminated or changed into groups having different structures and reactivity, the chemical-physical characteristics of the enzymes bound by such technique can be subjected to change deeply.

Cross-linking methods are based upon the covalent bonding of the molecules of the enzyme and bi- or multi-functional reactants so that threedimensional reticular aggregates completely insoluble in water are formed without using insoluble substrates. The method provides the addition of an appropriate quantity of cross-linking agent to an enzymatic solution under the most suitable conditions to form the insoluble derivative. The best conditions to achieve a good insolubility and to maintain the enzyme activity unchanged are unfortunately determined each time by a series of experimental tests. Such reactants are, for example: compositions including carbonyl groups adapted to react with the amino-group of L-lysine, L-histidine, L-tyrosine, L-arginine, L-cysteine; isocyanate adapted to react with the primary aminogroups; iodoalkanes adapted to react with the nucleophilic groups; iodoacetamides adapted to react with L-cysteine. Among such compositions the glutaraldehyde is mostly used. The best conditions to achieve a good insolubility efficiency and to maintain at the same time a considerable enzyme activity depend on the balance of factors such as concentration of the enzyme and the cross-linking agent, pH, ionic force, temperature, and reaction time. The disadvantages of such preparation method essentially consist both in the difficulty of controlling the intermolecular cross-linking which can form large enzyme aggregates having a high activity and in that a gelatinous structure is formed which cannot assure a good mechanical resistance and then a good flow characteristic in the continuous processes.

The physical absorption of the enzyme is carried out by mixing it with the substrate under suitable conditions. Subsequently, after a convenient period of time is elapsed, the enzymatic insoluble compound is separated from the starting material by centrifugation or filtration. As no chemical reaction occurs in such method of preparation, the composition of the enzymes does not change. The absorption depends on variables such as pH, solvent, ionic force, enzyme concentration, absorbent quantity, temperature. The greatest influence on the enzyme absorbed on a solid substrate is due to the concentration of the enzyme exposed per surface unit of the substrate during the linking process. The main drawback of such preparation method is that the bonding forces between enzyme and substrate are generally weak so that the enzyme can be desorbed in use. As a consequence, the mean life of such preparations may be short so that they cannot be used in long-time processes. The generally used substrates are: alumina, activated coal, clays among which bentonite, collagen, glass, hydroxylapatite and diatom dust are mainly used. Enzymes can also be bound by physical absorption onto materials having some affinity therewith, which is achieved by means of a derivatization of the substrate.

Methods leading to the ionic bonding are mainly based upon ionic interactions between the enzymatic protein and the solid substrate having residues adapted to exchange ions. Bonds due to the Van der Waals forces and ionic bonds cooperate to the formation of the resulting compounds. The main difference between such preparation methods and those based upon the physical absorption of the proteins consists in the bonding force between enzyme and substrate. As in the case of the preparation of the absorption compounds, also in the above preparation the compound is formed by contacting the substrate with the enzyme solution under softer reaction conditions than those of covalent bonding. The used substrates are generally polymers or compositions used in ion-exchange chromatography; they are organic substrates including residues adapted to exchange cations and anions. Also inorganic substrates, especially silica, to which ionic residues have been applied, can be used. Generally, the organic substrates are derivative of polysaccharides, in particular cellulose and dextrans, and polystyrene polymers. The compositions used to form the ion-exchanger substrates include: anion-exchanger compounds such as amino compounds, guanidine compounds, a.s.o. (for example, DEAE-, TEAE-, ECTEOLA-compounds), and cation-exchanger compounds having sulfuric, phosphoric and carboxylic groups.

The complexing with transition metals is based upon the chelating properties of the transition metals, in particular titanium and zirconium. The enzymes are made insoluble by activation of molecular groups at the surface of some substrates through such metals. The nucleophilic groups (—OH, —NH$_2$, —SH, a.s.o.) are good bonding agents for the transition metals, and therefore such metals can carry out the complexing both of the polymer and the enzyme. Substrates such as cellulose and silica have hydroxil groups acting as bonding agents adapted to substitute other agents. For such reason enzymes having in their molecule the alcoholic hydroxyl groups of L-scrine and L-threanine, the free sulfhydryl groups of L-cysteine, and the $\epsilon$-aminogroups of L-lysine can be bound by such method. Besides organic substrates such as cellulose and chitin also inorganic substrates such as silica and glass wool have been used but in the latter case the results have not ever been good. Generally, such method allows high specific activities of the compounds to be held, however, the continuous activity of such compounds has a variable stability.

The covalent bonding for binding enzymes to organic and/or inorganic substrates is the most complex among the techniques leading to the bonding between the two above mentioned components as the reaction conditions for the bonding are generally harder and the manipulations to be carried out are more complicated. What is important in such preparations is that the aminoacids of the enzymes essential for the catalytic activity are not involved in the bonding with the substrate. Sometimes the protection has been obtained by the addition of the substrate or a competitive inhibitor of the enzyme activity to the reaction mixture. The main factors which have to be considered in the preparation of the bound enzymes by means of a covalent bond are three: the functional groups of the proteins which can form the covalent bond under soft conditions; the kind of reaction between enzyme and substrate; the substrate to which a functional group adapted to bind the enzyme has been added. The easiest way for obtaining insoluble derivatives of enzymes and substrates is that the enzyme react in a solution upon the substrate already including the suitable reactants but this is only seldom possible because the substrate does not generally include them. In fact the substrate materials which are mostly used include in most cases hydroxyl groups, carboxyl groups, amino groups, and amide groups, and these groups should be activated by preliminary reactions with the aminoacid residues of the enzymes.

The entrapping methods are based upon the mixing of the enzymes with the latex of a polymer matrix or upon the storing thereof within semipermeable membranes having pores which are small enough to prevent proteins from going lost and at the same time large enough to allow substrates and products to pass through. Such methods can be applied to any enzyme having not very neutralized activities at least in comparison with the methods requiring chemical reactions.

Gel entrapping methods are based upon the enzyme entrapping within the interstitial spaces of cross-linked polymer gels insoluble in water. The polymer reticulum can be obtained by monomer, oligomer or polymer precursors by changing the solubility variables such as solvent, temperature, ionic force, and pH.

A different binding method leading to the entrapping of the enzyme into micro-cavities is the physical entrapping of an enzyme by dissolving a polymer adapted to form fibers (for example cellulose triacetate) in an organic solvent insoluble in water (for example, chloroform, methylene chloride, carbon tetrachloride) and by emulsifying such solution with the acqueous solution of the enzyme. The solution is poured in a liquid coalescent (for example, toluol or petroleum ether) which precipitates the emulsion under the form of a filament including microdrops of enzymatic solution. However, such preparation is limited to enzymes acting on substrates having a low molecular weight because of the difficulty due to the steric hindrance of the large substrates. Other problems originate from the necessity of using liquids insoluble in water as solvent of the polymer.

The enzymes can also be entrapped within microcapsules prepared along with organic polymers. The membranes enclosing the enzymes are semipermeable in comparison with substrate and products. The advantages of such method essentially consist in that the surface area exposed to the reaction is high and the volume in which the reaction occurs is small, that several enzymatic activities can be bound at the same time, and that the enzymes can be kept in their soluble state. The main disadvantages consist, however, in that such method cannot be applied to enzyme activities which catalyze reactions on substrates of high molecular weight, and that the disactivation may occur during the preparation.

SUMMARY OF THE INVENTION

The method in accordance with the present invention is different from the above mentioned methods in that it provides the absorption of biological catalytic activities of any kind onto an inert material of non-biological nature which is made of expanded clay having the following characteristics of:

being adapted to be confined in well-delimitated regions of the space so as to form an independent solid phase which can be removed from the system, if desired;

being porous enough as to allow the biological catalytic activities to be effectively absorbed;

being produced in several sizes having different porosities;

maintaining an inner complex cavity structure;

being resistant to compressive stress;

being adapted to stay under hydrous state for long time;

being made of material of argillaceous origin;

being subjected to sintering processes.

The latter aspect is essential for the preparation of the bound catalyst. In fact, even if the absorption of the biological catalytic activities is being studied for many years in the literature, especially as far as the various types of clay and the cationic substitutions on the same is concerned, the effect of any heat treatment on the absorbing property has not hitherto been considered.

From the experiments of the inventors it has been found that, in case of sintered expanded clay, the acquired chemical-physical properties allow it to be almost immediately used in the catalyst preparation process. The sintering modifies the specific surface, the bulk density, the hydration conditions, the micro- and macropores percentage, and the resistance to compressive stress, thus assuring very high absorbing capability and resistance to the desorption of the biological catalytic activities.

As known, an expanded clay is a granulated material, the single grain of which are formed of a hard and resistant outer skin enclosing an inner, very light cell structure formed of a lot of small cells non-communicating with one another; the size of grains ranges between 0 and 20 mm. The expanded clay is provided by baking special clays the melting point of which is between 1100° and 1250° C. according to the components thereof. Reactions occur in such temperature range among the components of the clays adapted for the production of expanded clay, which develops gases. Such gases which develop within the viscous material (it should be noted that the material is almost at the melting point) cause the mass to expand. If such expansion occurs in the interior of the grains rolling within a rotating tube, the end product will be an almost spherical grain covered by a compact skin (due to the rotation of the grain above one another) having an inner cell structure.

Expanded clay known under the trademark LECA was used in the examples of the invention. Such product is manufactured as follows:

Raw material for LECA is extracted from quarries of clay bodies and weathered for several months. Weathering makes clay more uniform and able to be worked. The clay is then worked by special machines and stored in sheds from which it is taken out continuously to be fed to the granulator and then to the oven. The granulator serves to determine the average size of the grains at the output of the oven. The oven is of the rotating type with reverse-current heating and is divided in two branches; drying and baking branches. The two branches are coaxial to each other. They rotate at different speeds so that the clay is fed at different rates according to whether it is in the drying step or in the expansion step. Special equipment are included in the oven with the function to promote the heat exchange between combustion gas and clay and to influence the provision of grains at different sizes. The latter function is particularly important for users because the size of the grains should have a variable granulometry and not be about a single value.

The material is at 1150° C. in the expansion area and afterward comes out of the oven and cooled at about 100°–150° C. in an air cooler. The cooling air is fed to the oven in order to recover heat. The material after cooling is fed to the storage from which it is taken out to be screened in the different granulometries.

The type of biological catalytic activities which can be used is limited only by the availability of the same in the nature as they may also include natural cells or cells modified by biotechnological processes, natural or modified microorganisms, organelles or subcellular elements. This assures that the problem of the degradation, transformation and use of the residues, or other compositions which cannot be considered as residues, can on principle be solved independently of the nature and composition of the substrate by a further development and adaptation. This also allows a variety of materials to be used by only changing slightly the parameters of the preparation of the product which is flexible and easy to modify in accordance with the requirements.

The biological catalytic activities of interest are absorbed in the liquid phase on the sintered expanded clay after being previously dissolved in a buffer solution of suitable pH and molarity.

The obtained product can be in turn entrapped within a link of biologically inactive compositions resisting degradation and formed by polymerization and/or copolymerization of simple or complex phenolic molecules, (polyhydroxybenzenes) which is more convenient from the economic point of view and responsive to the characteristic of the natural compositions than a link formed, for example, by copolymerization of acryloamide and bisacryloamide.

Catechol, pyrogallic acid, resorcinol or similar phenolic compositions can be used as phenolic monomers being adapted to generate radicals or ions stabilized by resonance and involving aromatic structures.

Advantageously, during the phenolic linking, biological catalytic activities can be copolymerized together with such link so that the link itself is formed by active and non-active catalytic parts which are protective against degradation.

The copolymerization of the phenol and the catalytic activity (one or more than one) can take place:

by enzyme catalysis (for example by laccase, tyrosinase, poroxidase and hydrogen peroxide) adapted to promote the formation of radicals and/or ions; by inorganic catalysis (for example by adding $M_nO_2$), ammonium persulfate or other catalysts so as to provide a varying proportion from 1:1:0.01 to 1:100:2500 among weight in grams of inorganic compound, weight in grams of phenolic compound and units of biological catalytic activity), and further by organic catalysis (for example by adding TEMED, light-activated tetramethylethyldiamine or other organic catalyst so as to provide a varying proportion from 0.1:1:0.01 to 0.1:100:2500 among weight in grams of organic compound, weight in grams of phenolic compound and units of biological catalytic activity.

Alternately or at the same time, further enzyme activities can be linked by polyfunctional compounds to the preceding preparation so that such activities can freely fluctuate in the environment.

If necessary, a combined system formed of microorganisms and bound enzymes can be used. This chain of catalytic material of biological kind appears as a succession of layers (only one layer may be provided) surrounding the substrate, thus forming sintetically metabolic ways adapted to operate on different, simple and complex residues.

A further feature of the invention is that of catalyzing reactions having molecule of different molecular weight as substrate. In fact, the described method allows the biological catalytic activities both outside and inside the system to be bound, in the latter case the inflow of the substrates by diffusion through the links is provided and controlled in accordance to the size of the links.

From the foregoing the method of the invention provides in whole or in part the following steps:

a) preparing a certain quantity of sintered expanded clay having a porosity of 25% to 75%;

b) preparing one or more liquid phases formed of a buffer solution having suitable pH and molarity and containing the biological catalytic activities of interest;

c) absorbing such solution on a substrate of sintered expanded clay;

d) preparing an acqueous phase containing a radical catalyst of biological kind (peroxidase and $H_2O_2$, laccase, tyrosinase, a.s.o.) or other kind (manganese dioxide, ammonium persulfate, TEMED, a.s.o.);

e) preparing an acqueous phase containing catechol and/or pyrogallic acid and/or resorcinol and/or similar phenolic compositions being adapted to provide radicals stabilized by resonance and involving aromatic structures;

f) adding said liquid phases to the preparation of phase c) in order to obtain a polymer and/or a copolymer of molecules of phenolic kind cross-linked to the bilogical catalytic activity at the surface of the clay particles;

alternately:

g) adding to preparation of phase a) a radical catalyst prepared as in phase d) of one or more phenolic compositions prepared as in phase e) and one or more biological catalytic activity prepared as in phase b) to provide a copolymer of one or more biological catalytic activities and phenolic compounds, which copolymer is cross-linked on sintered expanded clay.

The weight ratio between phenolic monomer and units of biological catalytic activities ranges from 1:0.01 to 1:250.

DESCRIPTION OF THE PREFERRED EMBODIMENTS

Figure 1:
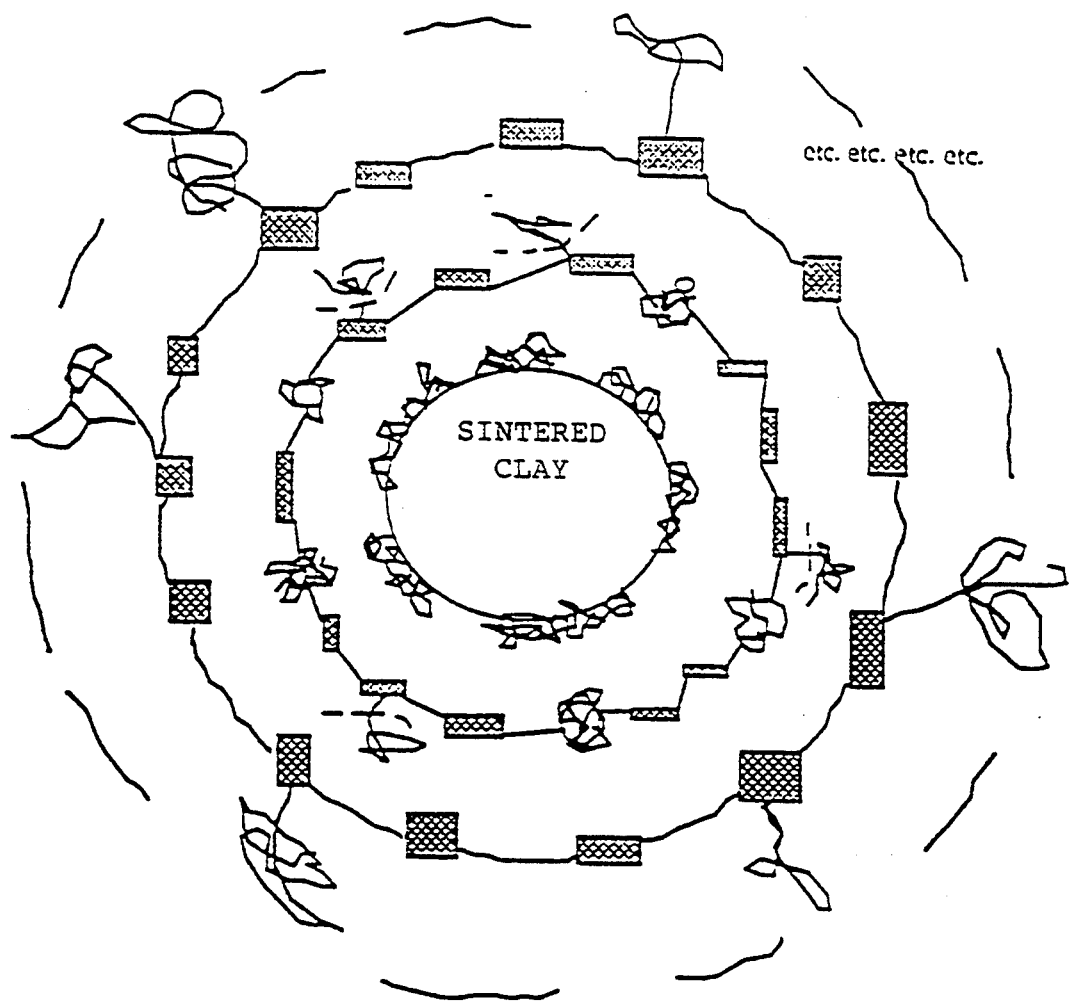
FIG. 1 illustrates a diagram of the distribution of the biological catalytic activities on the particles of sintered clay.
Figure 1:
Figure 1:
Figure 1:
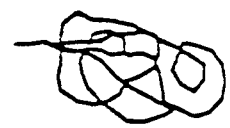

Further features of the present invention will be more readily apparent from the following examples of the invention showing by illustrative, non-limitative way the features of the products and some uses thereof.

EXAMPLE 1

Binding of acid phosphatase to sintered clay and preservation of its activity in the time.

The substrate formed of sintered clay (for example LECA by Laterlite) of different sizes was washed with 1N NaOH and then with distilled $H_2O$ until the washing water gave neutral reaction. It was dried then in oven at 110° C. 10 ml of a solution of acid phosphatase (extracted from wheat germ and having the activity of 2.3 EU/mg) purchased from the Company Fluka and obtained by dissolving 0.9 mg of enzyme in a buffer of 10 ml of 0.5M acetate at pH 4.75, was added to 10 grams of said material in a flask. The total quantity of enzyme to be absorbed on to the substrate was 2.07 EU corresponding to 0.207 EU per gram of sintered clay. The reaction mixture was placed into a refrigerator at 5° C. overnight. After this period of time the acid phosphatase bound to the sintered clay was washed three times with a buffer of 0.5M acetate at pH 4.75, and the washing water was collected to determine the non-bound acid phosphatase activity. The preparation was stored in a refrigerator at 5° C. Each time a test to ascertain the bound activity of the acid phosphatase had to be effected, the preparation was removed from the refrigerator, washed with a buffer of 0.5M acetate at pH 4.75, and placed into the reaction mixture. At the end of the test the preparation was washed again with a buffer of 0.5M acetate at pH 4.75 and stored into the refrigerator at 5° C. till a new test. The determination of the activity of the preparation was carried out by adding 1 ml of p-nitrophenylphosphate (PNP) at the concentration of 1000 $\mu$g/ml and 4 ml of a buffer of 0.5M acetate at pH 4.75 to 10 grams of the preparation. The quantity of the product p-nitrophenol (PNF) was determined after 3 hours of reaction at 37° C. by adding 1 ml of 0.5M $CaCl_2$ and 4 ml of 0.5N NaOH to 1 ml of the reaction mixture. After the development of the coloration the solution was passed into the spectrophotometer at 398 m$\mu$ against a white body. This was obtained by reacting 1 ml of PNP and 4 ml of a buffer of 0.5M acetate at pH 4.75 for three hours at 37° C. on a quantity of sintered clay corresponding to the active catalytic preparation. 1 ml of 0.5M $CaCl_2$ and 4 ml of 0.5N NaOH was added to 1 ml of such mixture. The quantity of PNF was determined by a calibration curve.

TABLE 1

| Activity of the acid phosphatase bound to sintered clay in the time. | | | |
|---|---|---|---|
| Time (days) | Residual activity (%) | Time (days) | Residual activity (%) |
| 0 | 87 | 119 | 59 |
| 2 | 85 | 153 | 71 |
| 8 | 100 | 253 | 61 |
| 20 | 98 | 320 | 43 |
| 35 | 80 | 389 | 33 |
| 43 | 69 | 442 | 22 |
| 55 | 61 | 504 | 25 |

In Table 1 data relative to the activity of the acid phosphatase bound to sintered clay are listed. In this table the residual activity is calculated as a percentage of the maximum measured activity, said residual activity being determined after 8 days from the preparation. The quantity of acid phosphatase bound to sintered clay corresponded to 7.3% of that contained in the buffer used for its preparation.

EXAMPLE 2

Influence of keeping at room temperature on the activity of the acid phosphatase bound to sintered clay.

A test with the acid phosphatase bound to sintered clay and prepared as in Example 1 was carried out by keeping the preparation over the duration of the test at room temperature instead of in the refrigerator at 5° C. All analysis and detection methods are similar to those described in Example 1.

TABLE 2

Activity of the acid phosphatase bound to sintered clay in the time.

| Time (days) | Residual activity (%) | Time (days) | Residual activity (%) |
|---|---|---|---|
| 0 | 82 | 153 | 45 |
| 2 | 81 | 222 | 47 |
| 8 | 100 | 254 | 33 |
| 13 | 84 | 320 | 31 |
| 20 | 80 | 389 | 24 |
| 55 | 73 | 442 | 27 |
| 119 | 43 | 504 | 22 |

In Table 2 the results of such test are listed. The percentages are calculated on the base of the maximum activity detected after 8 days from the date of preparation.

EXAMPLE 3

Restoring of the acid phosphatase activity of a land partially sterilized by heating at 150° C. by the addition of acid phosphatase bound to sintered clay.

After having taken earth from the soil classed as sandy loam according to the FAO's nomenclature, dried in the atmosphere, sieved to provide particles of maximum size up to 2 mm, and partially sterilized by heating at 150° C. for 5 hours, 5 grams were weighed to which 5 grams of the preparation of Example 1 were added. 1 ml of p-nitrophenilphosphate (PNP) dissolved in a buffer of 0.5M acetate at pH 4.75 and 10 ml of a buffer of 0.5M acetate at pH 4.75 were added to 10 grams of the mixture. After stirring for 3 hours at 37° C. the reaction mixture was filtered and 1 ml thereof was taken out. 1 ml of 0.5M CaCl$_2$ and 4 ml of 0.5N NaOH was added to said 1 ml of the mixture. After 30 minutes the solution was read at 398 m$\mu$. The results are shown in Table 3. In such Table there are also shown the activity of 5 grams of acid phosphatase bound to sintered clay, the activity of acid phosphatase of 5 grams of the soil, and the activity of the acid phosphatase of 5 grams of the partially sterilized soil. The acid phosphatase activity of the partially sterilized soil was restored by the bound activity by about 40%.

TABLE 3

Acid phosphatase activity of the soil, activity of the enzyme bound to sintered clay, and activity of the mixture thereof.

| Preparation | Activity (optical density at 398 m$\mu$) |
|---|---|
| Non-sterilized land | 0.643 |
| Partially sterilized land | 0.277 |
| Bound phosphatase | 0.258 |
| Bound phosphatase + partially sterilized land | 0.571 |

EXAMPLE 4

Absorption of the $\beta$-glucosidase on to sintered clay and preservation of its activity in the time.

The substrate formed of sintered clay of several sizes was washed with 1N NaOH and distilled H$_2$O until the washing water gave neutral reaction, then it was dried in oven at 110° C. 100 ml of a solution of $\beta$-glucosidase (extracted from sweet almond paste and having the activity of 4.4 EU/mg) purchased from the Company BDH and obtained by dissolving 50 mg of enzyme in 250 ml of a buffer of 0.1M acetate at pH 5.0, was added to 100 grams of the above material in a flask. The total quantity of enzyme to be absorbed on the substrate was 8.8 EU corresponding to 0.88 EU/gram of sintered clay. The reaction mixture was reacted in a refrigerator at 5° C. overnight. After this period of time the $\beta$-glucosidase bound to sintered clay was washed with a buffer of 0.1M acetate at pH 5.0, and the washing water was collected in order to determine the non-absorbed $\beta$-gluosidase activity. The preparation was stored in a refrigerator at 5° C. Each time a test to ascertain the bound $\beta$-glucosidase activity had to be effected, the preparation was removed from the refrigerator, washed with a buffer of 0.5M of acetate at pH 5.0, and placed into the reaction mixture. At the end of the test the preparation was washed again with a buffer of 0.1M acetate at pH 5.0 and placed into the refrigerator at 5° C. till a new test. The determination of the activity of the preparation was carried out by adding 4 ml of salicin at the concentration of 1% in a buffer of 0.1M acetate at pH 5.0 to 100 milligrams of the preparation. After 1 hour incubation at 37° C. the reaction mixture was separated from the solid phase and brought for 5 minutes at 100° C., then placed in ice until the room temperature was reached. After such period of time 0.1 ml was taken and analyzed for the reducing sugars according to the method of Nelson and Somogyi by a readout with a spectrophotometer at 520 m$\mu$ against a white body. This was obtained by contacting at 37° C. for 1 hour 4 ml of salicin at the concentration of 1% in a buffer of 0.1M acetate at pH 5.0 with a quantity of sintered clay corresponding to the activated enzyme preparation, and following the same procedure as before. The quantity of reducing sugars were calculated by a calibration curve drawn each time.

TABLE 4

Activity of the $\beta$-glucosidase bound to sintered clay in the time.

| Time (days) | Residual activity (%) | Time (days) | Residual activity (%) |
|---|---|---|---|
| 0 | 86 | 49 | 94 |
| 2 | 89 | 84 | 95 |
| 8 | 87 | 102 | 69 |
| 18 | 100 | 138 | 71 |
| 35 | 91 | 194 | 36 |

In Table 4 data relative to the activity of the $\beta$-glucosidase bound to sintered clay are listed assuming as a maximum the activity measured after 18 days from the beginning of the test. The quantity of glucosidase bound to sintered clay corresponds to 16.2% of that contained in the buffer used for the preparation.

EXAMPLE 5

Activity of the $\beta$-glucosidase bound to sintered clay after storing at room temperature for some time.

One hundred grams of $\beta$-glucosidase bound to sintered clay was prepared as described in Example 4.

Such preparation was stored at room temperature and 10 grams thereof was taken at predetermined time in order to carry out the test of the duration of the activity measured as in Example 4. In Table 5 the results of the test are listed.

TABLE 5

Activity of the β-glucosidase bound to sintered clay and stored at room temperature for different times.

| Storage time (days) | | | | | |
|---|---|---|---|---|---|
| 16 | | 26 | | 43 | |
| Time (days) | Activity (%) | Time (days) | Activity (%) | Time (days) | Activity (%) |
| 0 | 85 | 0 | 100 | 0 | 100 |
| 10 | 100 | 17 | 86 | 14 | 81 |
| 27 | 94 | 31 | 95 | 49 | 54 |
| 41 | 99 | 66 | 96 | 67 | 70 |
| 76 | 100 | 84 | 86 | 103 | 51 |
| 94 | 80 | 120 | 79 | 159 | 49 |
| 130 | 92 | 176 | 47 | — | — |
| 186 | 64 | — | — | — | — |

EXAMPLE 6

Restoring of the β-glucosidase activity of a land sterilized by heating at 150° C. by means of the addition of β-glucosidase bound to sintered clay.

After having taken earth from the soil classed as sandy loam according to the FAO's nomenclature, dried in the atmosphere, sieved to provide particles of maximum size up to 2 mm, and sterilized by heating at 150° C. for 48 hours, 5 grams were weighed to which 5 grams of the preparation of Example 4 were added. 4 ml of salicin at the concentration of 1% in a buffer of 0.1M acetate at pH 5.0 and 6 ml of a buffer of 0.5M acetate at pH 5.0 were added to 10 grams of the mixture. After stirring for 1 hour at 37° C. the reaction mixture was filtered and 0.1 ml thereof was taken out. The reducing sugars were determined on the above quantity as in Example 4. The results are shown in Table 6. In such Table there are also shown the activity of the β-glucosidase bound to 5 grams of sintered clay of the tested soil. The activity of the β-glucosidase of the soil was increased by 6 times due to the addition of the insoluble preparation.

TABLE 6

β-glucosidase activity of the soil, activity of the enzyme bound to sintered clay, and activity of the mixture thereof.

| Preparation | Activity (optical density at 398 mµ) |
|---|---|
| Non-sterilized land | 0.062 |
| Partially sterilized land | 0.005 |
| Bound β-glucosidase | 0.297 |
| Bound β-glucosidase + partially sterilized land | 0.342 |

EXAMPLE 7

Absorption of cellulase onto sintered clay and preservation of its activity in the time.

The substrate formed of sintered clay of several sizes was washed with 1N NaOH and distilled $H_2O$ until the washing water gave neutral reaction. Finally it was dried in oven at 110° C. 100 ml of a solution of cellulase (extracted from Tricoderma viride and having the activity of 0.02 EU/mg) purchased from the Company BDH and obtained by dissolving 100 mg of enzyme in 200 ml of a buffer of 0.1M acetate at pH 5.0, was added to 100 grams of the above material in a flask. The total quantity of enzyme to be absorbed onto the substrate was 2.0 EU corresponding to 0.02 EU/gram of sintered clay. The reaction mixture was reacted in a refrigerator at 5° C. overnight. After this period of time the cellulase bound to sintered clay was washed three times with a buffer of 0.1M acetate at pH 5.0, and the washing water was collected in order to determine the non-absorbed cellulase activity. The preparation was stored in a refrigerator at 5° C. Each time a test to ascertain the activity of the bound cellulase had to be effected, the preparation was removed from the refrigerator, washed with a buffer of 0.1M of acetate ad pH 5.0, and placed into the reaction mixture. At the end of the test the preparation was washed again with a buffer of 0.1M acetate at pH 5.0 and stored into the refrigerator at 5° C. till a new test. The determination of the activity of the preparation was carried out by adding 5 ml of carboxymethil cellulose (CMC) at the concentration of 1% in a buffer of 0.1M acetate at pH 5.0, and 3 ml of a buffer of 0.1M acetate at pH 5.0 to 10 grams of the preparation. After 1 hour incubation at 37° C. the reaction mixture was separated from the solid phase and added to 1 ml of 0.5M NaOH. Then 1 ml was taken and analyzed for the reducing sugars according to the method of Nelson and Somogyi by a readout with a spectrophotometer at 520 mµ against a white body. This was obtained by contacting at 37° C. for 1 hour 5 ml of CMC at the concentration of 1% in a buffer of 0.1M acetate at pH 5.0 and 3 ml of a buffer of 0.1M acetate at pH 5.0 with a quantity of sintered clay corresponding to the activated enzyme preparation, and following the same procedure as before. The quantity of reducing sugars was calculated by a calibration curve drawn each time.

TABLE 7

Activity of the cellulase bound to sintered clay in the time.

| Time (days) | Residual activity (%) |
|---|---|
| 0 | 100 |
| 22 | 47 |
| 38 | 30 |
| 68 | 21 |
| 125 | 11 |

The activity of the bound cellulase corresponds to 5.25% of that contained in the enzyme solution used for the preparation of the bound cellulase.

EXAMPLE 8

Activity of the cellulase bound to sintered clay after storing at room temperature for some time.

One hundred grams of cellulase bound to sintered clay was prepared as described in Example 7. Such preparation was stored at room temperature and 10 grams thereof was taken out at predetermined time in order to carry out the test of the duration of the activity by comparing the latter with the activity of the cellulase bound to freshly prepared sintered clay as described in Example 7. In Table 8 the results of the test are listed.

TABLE 8

Activity of the cellulase bound to sintered clay and stored at room temperature for different times.

| Storing time (days) | | | |
|---|---|---|---|
| 22 | | 38 | |
| Time (days) | Activity (%) | Time (days) | Activity (%) |
| 0 | 100 | 0 | 100 |
| 16 | 42 | 14 | 40 |
| 30 | 26 | 51 | 16 |
| 67 | 9 | — | — |

EXAMPLE 9

Preparation and enzyme activity of a copolymer formed of pyrogallic acid and acid phosphatase by peroxidase and $H_2O_2$ and cross-linked onto $\beta$-gluocosidase absorbed onto sintered expanded clay.

Fifty grams of $\beta$-glucosidase bound to sintered clay were prepared as described in Example 4. 7.5 ml of a solution containing pyrogallic acid (25 mg/100 ml), 10 ml of a solution containing peroxidase (25 mg/250 ml) and 2.5 ml of 0.06% $H_2O_2$ were added to 5 grams of the above preparation. Then 5 ml of a solution of acid phosphatase (18 mg/200 ml of a buffer of 0.1M acetate at pH 5.0) was added to such preparation. After slow stirring for 2 hours the preparation was filtered and washed with distilled water, and then stored in refrigerator at 5° C. Both glucosidase and phosphatase activities of such preparation were measured at different time intervals, at the end of each of them the preparation was washed with distilled water and stored in refrigerator at 5° C. till the new test. The results of such tests performed as described in Examples 1 and 4 are listed in Table 9.

TABLE 9

Activity of $\beta$-glucosidase bound to sintered clay in the time, and activity of acid phosphatase copolymerized with pyrocatechol by peroxidase and $H_2O_2$.

| Time (days) | $\beta$-glucosidase residual activity (%) | Acid Phosphatase residual activity (%) |
|---|---|---|
| 0 | 87 | 75 |
| 2 | 100 | 100 |
| 8 | 85 | 78 |

EXAMPLE 10

Preparation and enzyme activity of a copolymer formed of pyrogallic acid and acid phosphatase by ammonium persulfate and cross-linked on $\beta$-gluocosidase absorbed onto sintered expanded clay.

Fifty grams of $\beta$-glucosidase bound to sintered clay were prepared as described in Example 5. 0.5 ml of a solution containing pyrogallic acid (25 mg/100 ml) and 10 ml of a solution containing persulfate (100 mg/100 ml) were added to 5 grams of the above preparation. Then 5 ml of a solution of acid phosphatase (18 mg/200 ml of a buffer of 0.1M acetate at pH 5.0) was added to such preparation.

After slow stirring for 1 hour the preparation was filtered and washed with distilled water, and then stored in refrigerator at 5° C. Both $\beta$-glucosidase and acid phosphatase activities of such preparation were measured at different time intervals, at the end of each of them the preparation was washed with distilled water and stored in refrigerator at 5° C. till the new test. The results of such tests performed as described in Examples 1 and 4 are listed in Table 10.

TABLE 10

Activity of $\beta$-glucosidase bound to sintered clay in the time, and activity of acid phosphatase copolymerized with pyrocatechol by peroxidase and $H_2O_2$.

| Time (days) | $\beta$-glucosidase residual activity (%) | Acid Phosphatase residual activity (%) |
|---|---|---|
| 0 | 83 | 78 |
| 2 | 100 | 100 |
| 8 | 85 | 64 |
| 9 | 88 | 71 |

EXAMPLE 11

Preparation and enzyme activity of a copolymer formed of catechol and $\beta$-glucosidase by manganese dioxide and cross-linked on sintered expanded clay.

A solution consisting of 1 ml of a solution of $MnO_2$ (100 mg/ml), 1 ml of a solution of catechol (250 mg/100 ml), and 5 ml of a solution of $\beta$-glucosidase obtained by dissolving 50 mg of enzyme in 250 ml of a buffer of 0.1M acetate at pH 5.0 was added to 5 grams of sintered expanded clay.

After slow stirring for 1 hour the preparation was filtered and washed with distilled water, and then stored in refrigerator at 5° C. The $\beta$-glucosidase activity of such preparation was measured at different time intervals, at the end of each of them the preparation was washed with distilled water and stored in refrigerator at 5° C. till the new test. The results of such tests performed as described in Example 4 are listed in Table 11.

TABLE 11

Activity of $\beta$-glucosidase copolymerized with catechol by MnO2 on sintered expanded clay in the time.

| Time (days) | $\beta$-glucosidase residual activity (%) |
|---|---|
| 0 | 98 |
| 2 | 100 |
| 12 | 87 |
| 27 | 81 |

EXAMPLE 12

Preparation and enzyme activity of a copolymer formed of pyrogallic acid and $\beta$-glucosidase by TEMED, cross-linked on sintered expanded clay.

A solution consisting of 30 $\mu$l of a solution of TEMED (80 mg/100 ml), 1 ml of a solution of pyrogallic acid (250 mg/100 ml), and 5 ml of a solution of $\beta$-glucosidase obtained by dissolving 50 mg of enzyme in 250 ml of a buffer of 0.1M acetate at pH 5.0 was added to 5 grams of sintered expanded clay.

After slow stirring for 1 hour the preparation was filtered and washed with distilled water, and then stored in refrigerator at 5° C. The $\beta$-glucosidase activity of such preparation was measured at different time intervals, at the end of each of them the preparation was washed with distilled water and stored in refrigerator at 5° C. till the new test. The results of such tests performed as described in Example 4 are listed in Table 12.

TABLE 12

Activity of $\beta$-glucosidase copolymerized with pyrogallic acid by TEMED on sintered expanded clay in the time.

| Time (days) | $\beta$-glucosidase residual activity (%) |
|---|---|
| 0 | 100 |
| 2 | 85 |
| 12 | 63 |
| 27 | 48 |

EXAMPLE 13

Restoring of the acid phosphatase activity of a land, sterilized by heating at 250° C., due to the addition of urban waste and acid phosphatase bound to sintered clay.

After having taken earth from the soil classed as sandy loam according to the FAO's nomenclature, dried in the atmosphere, sieved to provide particles of maximum size up to 2 mm, and sterilized by heating at 250° C. for 5 hours, 5 grams were weighed to which 5 grams of the preparation of Example 1 was added. 5 g of urban waste and 15 ml of a buffer of 0.5M acetate at pH 4.75 were added to 10 grams of the mixture. After stirring for 2 days at 37° C. the reaction mixture was filtered and 1 ml thereof was taken out. Inorganic phosphate was detected over a blank where sintered clay without acid phosphatase was added instead of acid phosphatase bound to sintered clay. The results are shown in Table 13.

TABLE 13

| Inorganic phosphate of the sterilized soil after the addition of 5 g urban waste and 5 g acid phosphase bound to sintered clay. | |
|---|---|
| Time | Inorganic phosphate (ug/g) |
| 2 | 1,7 |

The results are the average of 5 repetitions.

EXAMPLE 14

Decontamination of an agricultural land treated by herbicides by means of the addition of peroxidase bound to sintered expanded clay.

A test with two sets of samples was performed. Each sample was provided by adding 200 g of quartz to 50 g of soil. 20 micrograms/g soil of 2,4-dichlorophenoacetic acid (herbicide for wheat) was then added. The two sets were subjected to incubation at 25° C. into a climatic cell after addition to one of the two sets of 50 g peroxidase absorbed to sintered expanded clay according to the method of the present invention. After 10 days 50 seeds of durum wheat "CRESO" were added to both sets of samples upon being sure that the humidity of the soil was steady.

After 18 days the wheat plantlets were pulled up from the soil, dried and weighed. The results of the search are shown in Table 14.

TABLE 14

| Percent dry matter yield of wheat plantlets with and without peroxidase bound to sintered expanded clay. | |
|---|---|
| Test | Yield % |
| Wheat + peroxidase | 137 |
| Wheat − peroxidase | 100 |

Each test was repeated 5 times and the related data are the average value of the 5 tests.

Example 14 points out that the application of the substrate can also be extended to incidental noxious leakages.

EXAMPLE 15

Cleaning of a water conditioner from organic phosphates by the addition of acid phosphatase bound to sintered expanded clay.

Ten grams of acid phosphatase bound to sintered clay prepared as in Example 1 were put into a beaker together with an iron bar covered with polyethylene, and a steel disc provided with holes having a diameter of 1 mm was placed above them.

Then 50 ml of a solution from a cleaner for the treatment of waste water was added, and the mixture was incubated at 30° C. at constant stirring.

After 15 days of incubation 1 ml of the solution was taken out and the amount of inorganic phosphate contained therein was determined.

The detection of inorganic phosphate was carried out over a blank which was different because the sintered clay balls had not been formerly treated by acid phosphatase. The results of the experiment are shown in Table 15.

TABLE 15

| Amount of inorganic phosphates released by the addition of acid phosphatase bound to sintered clay. | |
|---|---|
| Time (Days) | Inorganic phosphate (ug/ml) |
| 0 | 0 |
| 15 | 2,3 |

The results are averages of 5 repetitions.

EXAMPLE 16

Oxidation of phenol by adding laccase absorbed by sintered expanded clay.

Ten grams of a preparation of laccase extracted from *Rhizoctonia praicola* and bound to sintered expanded clay according to the method of Examples 1, 4 and 7 were added to 50 ml of a solution containing 0, 1 ml phenol (100 ug/ml) and subjected to incubation at 25° C. for 0, 1 and 2 days. Each time 1 ml was taken out and the phenol was detected over a blank provided like that of the preceding Example except that the laccase had not been absorbed on the sintered clay.

The results of the experiment are shown in Table 16. Data are an average of 5 repetitions.

TABLE 16

| Amount of residual phenol (%) after addition of laccase bound to sintered expanded clay. | |
|---|---|
| Days | Residual phenol (%) |
| 0 | 100 |
| 1 | 48 |
| 2 | 17 |

We claim:

1. A method of binding enzymes to an insoluble sintered expanded clay support matrix, comprising the steps of:
    a) combining a solution of enzyme having biological catalytic activity with an insoluble sintered expanded clay support matrix whereby the support matrix absorbs the enzyme solution and the enzyme is bound to surfaces of the support matrix;
    b) combining the support matrix containing bound enzyme from step a with a solution containing an enzyme having biological catalytic activity different from the enzyme bound to the support matrix and a phenolic monomer selected from the group consisting of catechol, pyrogallic acid, resorcinol and mixtures thereof; and
    c) copolymerizing the enzyme and phenolic monomer combined with the support matrix in step b to form a layer of copolymer of enzyme and phenolic monomer on the support matrix containing bound enzyme.

2. The method of claim 1, wherein the sintered expanded clay has a porosity of 25% to 75%.

3. The method of claim 1, wherein the weight ratio between phenolic monomer and units of enzyme ranges from 1:0.01 to 1:250.

4. The method of claim 1, wherein the copolymer is formed by enzyme catalysis with an enzyme catalyst.

5. The method of claim 4, wherein the enzyme catalyst is laccase or tyrosinase, or peroxidase in combination with hydrogen peroxide.

6. The method of claim 1, wherein the copolymer is formed by inorganic catalysis with an inorganic catalyst.

7. The method of claim 6, wherein the inorganic catalyst is ammonium persulfate.

8. The method of claim 6, wherein the inorganic catalyst is manganese dioxide.

9. The method of claim 1, wherein the copolymer is formed by organic catalysis with an organic catalyst.

10. The method of claim 7, wherein the organic catalyst is N,N,N',N' tetramethyl-ethylene-diamine(TEMED).

11. The method of claim 2, wherein the weight ratio between phenolic monomer and units of enzyme ranges from 1:0.01 to 1:250.

12. An insoluble sintered expanded clay support matrix containing bound enzymes produced by the method of claim 1.

* * * * *

UNITED STATES PATENT AND TRADEMARK OFFICE
CERTIFICATE OF CORRECTION

PATENT NO. : 5,443,975
DATED : August 22, 1995
INVENTOR(S) : CERVELLI, et al

It is certified that error appears in the above-indentified patent and that said Letters Patent is hereby corrected as shown below:   On the title page:

Item [73] line 1, "Technologie" should be corrected to read -- Tecnologie --.

Signed and Sealed this

Twelfth Day of November, 1996

Attest:

BRUCE LEHMAN

Attesting Officer          Commissioner of Patents and Trademarks